United States Patent [19]

Wolf

[11] 4,124,374
[45] Nov. 7, 1978

[54] ALKYL-SUBSTITUTED CYCLOALKANAPYRAZOLE HERBICIDES

[75] Inventor: Anthony D. Wolf, Newark, Del.

[73] Assignee: E. I. Du Pont de Nemours and Company, Wilmington, Del.

[21] Appl. No.: 727,362

[22] Filed: Sep. 27, 1976

Related U.S. Application Data

[63] Continuation-in-part of Ser. No. 655,842, Feb. 6, 1976, abandoned.

[30] Foreign Application Priority Data

Apr. 13, 1976 [TW] Taiwan .................................. 6510765

[51] Int. Cl.² ..................... A01N 9/22; C07D 231/54; C07D 231/56
[52] U.S. Cl. ........................................ 71/92; 548/369; 544/175; 260/586 R
[58] Field of Search ....................... 260/310 R; 71/92; 548/369

[56] References Cited

U.S. PATENT DOCUMENTS

| | | | |
|---|---|---|---|
| 3,364,227 | 1/1968 | Robinson et al. | 71/92 |
| 3,646,059 | 2/1972 | Brantley et al. | 71/92 |
| 3,948,937 | 4/1976 | Johnson et al. | 71/92 |
| 4,008,249 | 2/1977 | Fischer et al. | 260/310 R |

OTHER PUBLICATIONS

Nunn et al., Chem. Abst., vol. 82, 1975, 170804a.
Bayer, Chem. Abst., vol. 60, 6957.
Jacquier et al., Chem. Abst., vol. 67, 1967, 43768g.
Ozolins, Chem. Abst., vol. 84, 1976, 90060f.

Primary Examiner—Natalie Trousof
Assistant Examiner—Jane T. Fan

[57] ABSTRACT

Herbicidal alkyl-substituted cycloalkanapyrazoles of the formula:

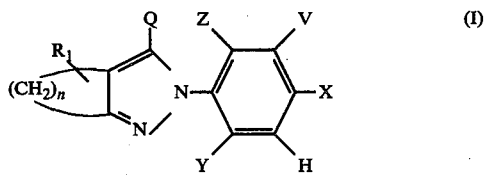

where
n is 3, 4 or 5;
$R_1$ is hydrogen or methyl;
Q is methyl;
X is fluorine, chlorine, bromine, iodine, cyano or methoxy;
Y is hydrogen, fluorine or chlorine;
Z is hydrogen or fluorine;
V is hydrogen, fluorine, chlorine or OR; and
R is alkyl of 1 to 4 carbon atoms; with the proviso that
 a. when n is 3, $R_1$ is hydrogen;
 b. when n is 5, $R_1$ is hydrogen, Y is hydrogen or fluorine, Z and V are hydrogen and X is fluorine, chlorine or bromine;
 c. when V is OR, X and Y are chlorine and Z is hydrogen;
 d. when V is fluorine or chlorine, X is fluorine, chlorine or bromine and Z is hydrogen.

Preferred for their higher activity or favorable cost or both are those compounds of formula I where, independently,
 1. $R_1$ is hydrogen and n is 4,
 2. Y is hydrogen or fluorine, V is hydrogen and Z is hydrogen.

Most preferred for their outstanding herbicidal activity are those compounds of formula I where n is 4, $R_1$ is hydrogen, X is fluorine, chlorine or bromine, Y is hydrogen or fluorine, V is hydrogen and Z is hydrogen.

40 Claims, No Drawings

ALKYL-SUBSTITUTED CYCLOALKANAPYRAZOLE HERBICIDES

RELATED APPLICATIONS

This application is a continuation-in-part of Ser. No. 655,842, filed Feb. 6, 1976, now abandoned.

BACKGROUND OF THE INVENTION

West German Application No. 1,948,793, dated Sept. 26, 1969, discloses a method for preparation of a broad general class of 4,5,6,7-tetrahydroindazoles which are useful intermediates in the preparation of pharmaceuticals, agricultural chemicals and corrosion inhibitors.

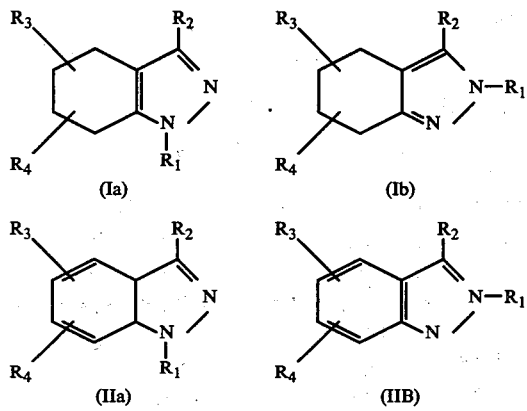

Specifically disclosed is the preparation of Compound Ib, where $R_2$, $R_3$, and $R_4$ are hydrogen and $R_1$ is phenyl, from Compound IIb (same substitution) by catalytic reduction. The preparation and fungicidal utility of the 2-(4-chlorophenyl)-1,2,4,5,6,7-hexahydroindazol-3(3H)-one is disclosed in Takeda Chem. Ind. Paper, Chem. Abs., 67, 11542h (1967):

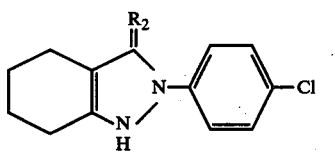

2-Aryl-4,5,6,7-tetrahydro-1-alkyl-1H-indazol-3(2H)-ones are claimed as antipyretics in Ger. 668,628 [assigned to P. Beierdorf & Co. AG, Chem. Abs., 33, 5131[2] (1939)] and U.S. P. 2,104,348 [assigned to E. R. Squibb Co., Chem. Abs., 32, 1869[1] (1938)].

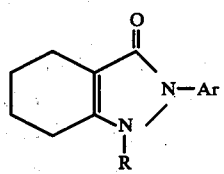

1-Phenyl-3,4-trimethylenepyrazolone is disclosed in U.S. Pat. No. 1,685,407 (1928) with utility as intermediate for making dyes and medicinal compounds. C. Mannich in Arch. Pharm. 267, 699–702 (1929) and in Brit. 260,577 describes the preparation of 1-phenyl-3,4-trimethylenepyrazolones.

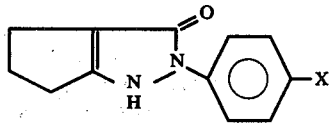

R. P. Williams et al. in J. Med. Chem. 13, 773 (1970) reports the preparation and evaluation as anti-inflammatory agents compounds of the following type:

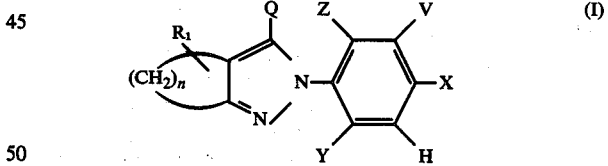

X = H, Br, F.

Although some of the compounds disclosed in the above-cited references are useful as agricultural products, none are taught to be herbicides, especially selective herbicides. The presence of undesired vegetation is very damaging to useful crops such as rice and wheat. In the current world situation, wherein food shortages are acute, it is most important not to lose a portion of a valuable crop such as rice or wheat. The presence of such undesired vegetation results in the loss of a significant portion of such crops. Thus, a need exists for a particularly effective herbicide which will destroy as much unwanted vegetation as possible without causing significant damage to the desired crops, e.g. rice.

According to the instant invention, compounds have been discovered which are highly active herbicides and yet cause minimal damage to certain desired crops, e.g. rice and wheat.

DESCRIPTION OF THE INVENTION

This invention relates to novel compounds of Formula I and their agricultural compositions, and to the method of use of these compounds for pre- and post-emergence control of undesirable vegetation, particularly barnyardgrass in rice:

(I)

where
 $n$ is 3, 4 or 5;
 $R_1$ is hydrogen or methyl;
 Q is methyl;
 X is fluorine, chlorine, bromine, iodine, cyano or methoxy;
 Y is hydrogen, fluorine or chlorine;
 Z is hydrogen or fluorine;
 V is hydrogen, fluorine, chlorine or OR; and
 R is alkyl of 1 to 4 carbon atoms; with the proviso that
 a. when $n$ is 3, $R_1$ is hydrogen;
 b. when $n$ is 5, $R_1$ is hydrogen, Y is hydrogen or fluorine, Z and V are hydrogen and X is fluorine, chlorine or bromine;
 c. when V is OR, X and Y are chlorine and Z is hydrogen;

d. when V is fluorine or chlorine, X is fluorine, chlorine or bromine and Z is hydrogen.

Preferred for their higher activity or favorable cost or both are those compounds of formula I where, independently,
1. $R_1$ is hydrogen and $n$ is 4,
2. Y is hydrogen or fluorine, V is hydrogen and Z is hydrogen.

Most preferred for their outstanding herbicidal activity are those compounds of formula I where $n$ is 4, $R_1$ is hydrogen, X is fluorine, chlorine or bromine, Y is hydrogen or fluorine, V is hydrogen and Z is hydrogen.

Specifically preferred for their outstanding herbicidal activity are:
2-(4-chloro-2-fluorophenyl)-3-methyl-4,5,6,7-tetrahydro-2H-indazole, m.p. 84.5°–87.5° C
2-(4-bromo-2-fluorophenyl)-3-methyl-4,5,6,7-tetrahydro-2H-indazole, m.p. 93°–96° C.

SYNTHESIS OF THE COMPOUNDS

The novel cycloalkanapyrazoles of Formula I are prepared in one step by the reaction of an arylhydrazine with the appropriate 2-acetylcycloalkanones as shown by the following Equation A:

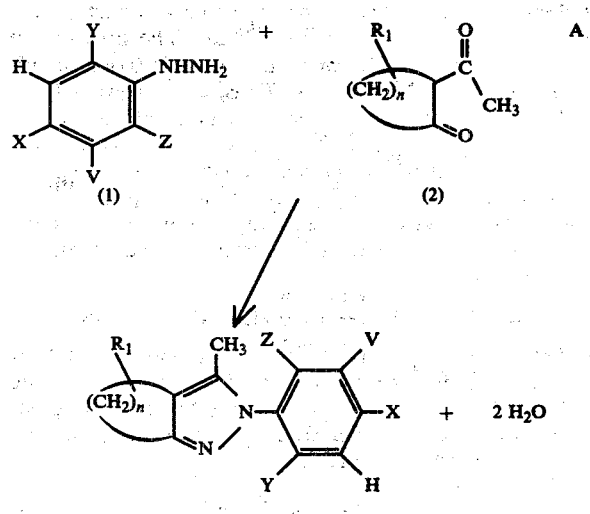

where:
$R_1$, $n$, X, Y, Z and V are as defined above.

The cycloalkanapyrazoles are prepared by combining the 2-acetylcycloalkanones (2) with an arylhydrazine (1) in an appropriate solvent, such as an aromatic hydrocarbon, i.e. xylene, toluene, or chlorobenzene, followed by azeotropic removal of the water formed by the reaction. An acid catalyst, i.e., acetic acid, p-toluenesulfonic acid, etc., facilitates the reaction. Generally the progress of the condensation can be followed by measuring the volume of water removed from the reaction. At reflux temperature, 0.5–24 hours are required.

The cycloalkanapyrazoles are isolated by solvent removal and crystallization of the resultant solid or oil from a hydrocarbon solvent, i.e. hexane, heptane.

The required 2-acetylcycloalkanones can be prepared as illustrated by Equation B. A related synthesis is described in *Organic Syntheses, Coll. Vol. V*, 533 (1973). Acetyl chloride is reacted in a chloroform solution with a 1-morpholino-1-cycloalkene in the presence of an equal molar quantity of anhydrous triethylamine. After 2-3 hours, the resultant reaction mixture is hydrolyzed with 20% aqueous hydrochloric acid. After neutralization, the 2-acetylcycloalkanones are isolated from the chloroform extracts.

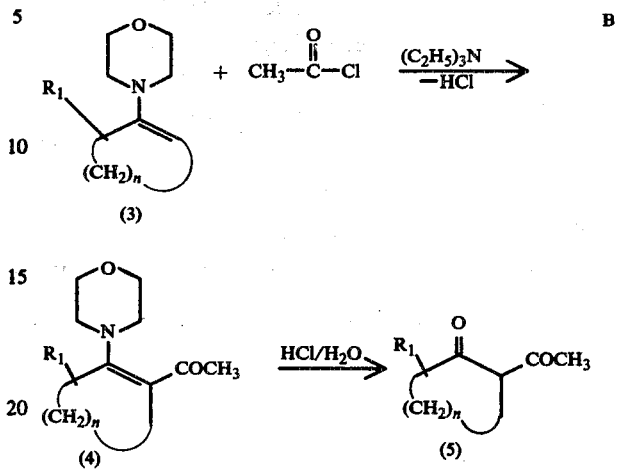

The use of enamines of 3-alkylcyclohexanones (3) ($n=4$) leads to a mixture of alkyl-substituted 2-acetylcyclohexanones. If this mixture is reacted with an arylhydrazine, a mixture of 4- and 6-substituted tetrahydroindazoles (where $R_1$ is as defined in Formula I) is produced (Equation C).

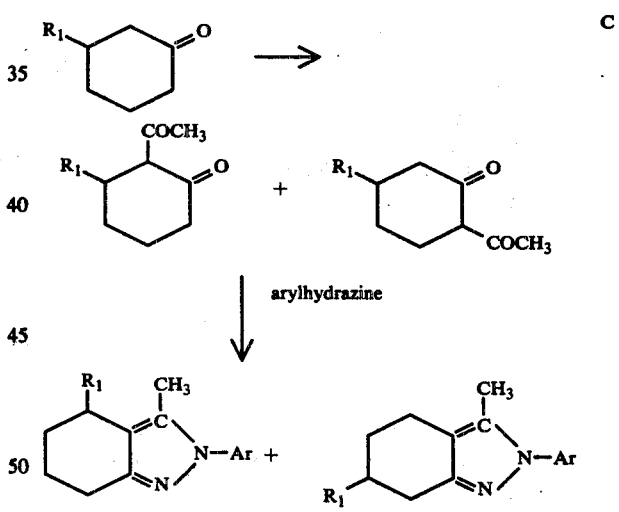

In the case of the 2- or 4-alkylcyclohexanones, the synthesis is more specific and predominately one isomer is produced, as summarized schematically in Equations D and E. 2-Alkylcyclohexanones product 7-alkyl-3-methyl-2-aryl-4,5,6,7-tetrahydroindazoles, and 4-alkylcyclohexanones produce 5-alkyl-3-methyl-2-aryl-4,5,6,7-tetrahydroindazoles.

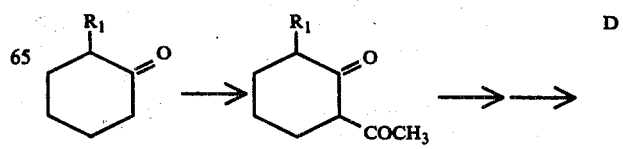

-continued

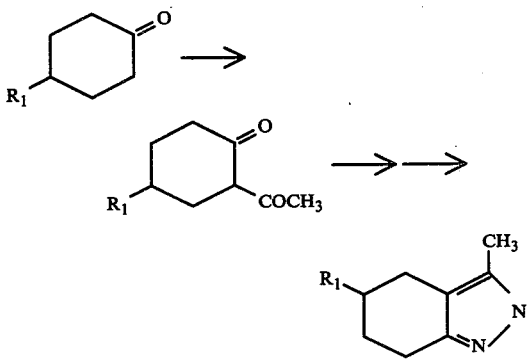

The preparation of arylhydrazine from anilines is well documented in the literature: G. H. Coleman, *Organic Syntheses, Coll. Vol. I*, J. Wiley & Sons, New York, p. 442 and H. Kindler et al., Fr. 1,419,092. The general procedure is illustrated in Equation F.

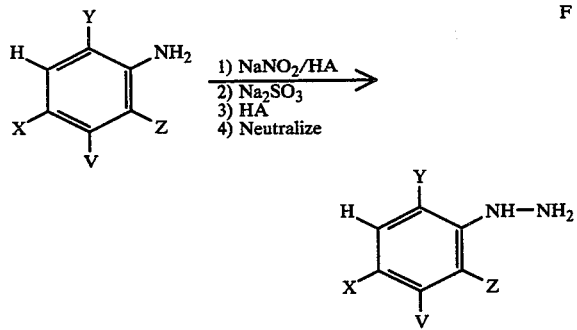

A = acid of ionization constant of at least $1 \times 10^{-7}$ e.g. $H_2SO_4$ or HCl The following examples further illustrate the method for synthesis of compounds of this invention. All parts are by weight and all temperatures are in degrees centigrade.

EXAMPLE 1

Preparation of 2-(4-chloro-2-fluorophenyl)-3-methyl-4,5,6,7-tetrahydro-2H-indazole

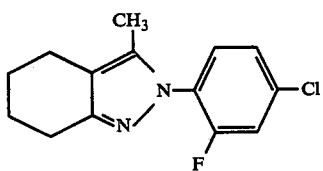

(a) Preparation of 4-chloro-2-fluoroaniline

Seventy-one parts of liquid chlorine were added to a solution of 140 parts of 2′-fluoroacetanilide in 500 parts glacial acetic acid, during one hour, at 25°–27° C, with icewater cooling. While stirring for 4 hours at 25°–27° C, 4′-chloro-2′-fluoroacetanilide precipitated. After collecting the product by filtration, the filtrate was poured over 2000 parts of ice. The resulting second portion of precipitated product was collected by filtration, combined with the first portion and recrystallized from 700 parts of methanol at −45° C to yield 119 parts of 4′-chloro-2′-fluoroacetanilide as white crystals melting at 152°–155° C.

A mixture of 119 parts of 4′-chloro-2′-fluoroacetanilide in 475 parts of ethanol and 200 parts of 37% hydrochloric acid was refluxed for 17 hours and the solvent removed under a reduced pressure of 300 mm.Hg to yield the moist, solid hydrochloride salt of 4-chloro-2-fluoroaniline.

The moist, solid hydrochloride salt of 4-chloro-2-fluoroaniline was cooled to 10° C in an ice-acetone bath and 50% aqueous sodium hydroxide was added dropwise, with stirring, until pH 11 was obtained. The resulting two-phase mixture was extracted four times; 500 parts of methylene chloride was used for each extraction. The combined organic extracts were dried with anhydrous sodium sulfate and the solvent removed under reduced pressure of 300 mm.Hg to leave 89 parts of light brown, oily 4-chloro-2-fluoroaniline, $n_D^{25} = 1.5541$.

(b) Preparation of 4-chloro-2-fluorophenylhydrazine hydrochloride

200 Parts of 4-chloro-2-fluoroaniline was dissolved in 80 parts of water and 34 parts of concentrated hydrochloric acid. The solution was cooled to 0°–10° C and 32.2 parts of 30% sodium nitrite was added dropwise maintaining the temperature of the reaction between 0°–10° C. After the addition of nitrite was completed, the solution was stirred for thirty minutes at 0°–10° C. The excess nitrite was destroyed by the addition of small amounts of sulfamic acid. When a negative test with sulfone reagent was obtained, the diazonium salt was ready for reduction. For a description see H. E. Fierz-David et al., *Fundamental Processes of Dye Chemistry* translated fromm 5th Austrian Ed. by P. W. Wittam, Interscience Publishers, Inc., New York, 1949, p. 243.

In a separate vessel 35.4 parts of sodium bisulfite and 32.2 parts of 30% sodium hydroxide solution were dissolved in 140 parts of water. The solution was heated to 40° C. The diazonium salt was added to he bisulfite solution over a period of about 1 hour. The mixture was heated to 70° C and 0.03 parts of sodium bisulfite was added. The pH was adjusted to 1.2 with 30 parts of concentrated hydrochloric acid; then an additional 90 parts of concentrated hydrochloric acid was added. The reaction mixture was heated for 1.5 hours at 70° C, cooled slowly, and stirred overnight at room temperature.

Purification was achieved by heating the reaction mixture to 70° C and filtering. The filtrate was cooled to 10° C at which time the 4-chloro-2-fluorophenylhydrazine hydrochloride precipitated. This product was filtered and dried to yield 10.7 parts of yellow crystalline solid, m.p. 223° C.

(c) Preparation of 2-(4-chloro-2-fluorophenyl)-3-methyl-4,5,6,7-tetrahydro-2H-indazole A solution of 19.7 parts of 4-chloro-2-fluorophenylhydrazine and 14.0 parts of 2-acetylcyclohexanone in 50 parts of xylene and 1 part of glacial acetic acid were refluxed for 24 hours with a Dean Stark trap to collect the water formed. The xylene was distilled from the mixture. The residual oil was dissolved in arm hexane solution. On cooling, 6.2 parts of crude product was obtained. Recrystallization of this product yielded white crystals of 2-(4-chloro-2-fluorophenyl)-3-methyl-4,5,6,7-tetrahydro-2H-indazole, melting point 84.5°–87.5° C; ir bands (1570 cm$^{-1}$, 905 cm$^{-1}$, 822 cm$^{-1}$).

Using the procedure of Example 1 with 2-acetylcyclohexanone, the appropriate arylhydrazine the following compounds of Formula I are prepared:

| Y | X | V | Z | M.P. |
|---|---|---|---|---|
| H | Cl | H | H | 67–71° |
| H | Br | H | H | 99–103° |
| H | CH$_3$O | H | H | ir bands: 1580, 840 cm$^{-1}$ |
| H | CN | H | H | 115–118° |
| Cl | Cl | H | H |  |
| F | Br | H | H | 93–96° |
| F | CH$_3$O | H | H |  |
| F | CN | H | H |  |
| F | F | H | H |  |
| H | F | H | H |  |
| F | Cl | H | F |  |
| F | I | H | H | 95–98° |
| H | I | H | H | 110–115° |
| Cl | Cl | Cl | H |  |
| F | F | F | H |  |
| Cl | Cl | OCH$_3$ | H | 125–130° |
| Cl | Cl | OC$_2$H$_5$ | H |  |
| Cl | Cl | OCH(CH$_3$)$_2$ | H | ir band: 1590 cm$^{-1}$ |
| Cl | Cl | OCH$_2$CH$_2$CH$_3$ | H |  |
| Cl | Cl | OCH$_2$CH$_2$CH$_2$CH$_3$ | H |  |
| Cl | Cl | O—CH$_2$CH(CH$_3$)$_2$ | H |  |

Using the procedure of Example 1 with a methyl-substituted 2-acetylcyclohexanone, and the appropriate arylhydrazine, the following compounds may be prepared:

| R | Y | X | V | Z |
|---|---|---|---|---|
| 7-CH$_3$— | H | Cl | H | H |
| 7-CH$_3$— | H | Br | H | H |
| 7-CH$_3$— | H | CH$_3$O | H | H |
| 7-CH$_3$— | H | CN | H | H |
| 7-CH$_3$— | Cl | Cl | H | H |
| 5-CH$_3$— | F | Br | H | H |
| 5-CH$_3$— | F | CH$_3$O | H | H |
| 4-CH$_3$— | F | CN | H | H |
| 6-CH$_3$— | F | F | H | H |
| 4-CH$_3$— | F | I | H | H |
| 6-CH$_3$— | H | I | F | H |
| 6-CH$_3$— | F | F | H | F |
| 4-CH$_3$— | Cl | Cl | Cl | H |
| 4-CH$_3$— | F | F | F | H |
| 5-CH$_3$— | Cl | Cl | OCH$_3$ | H |
| 5-CH$_3$— | Cl | Cl | OC$_2$H$_5$ | H |
| 6-CH$_3$— | Cl | Cl | OCH(CH$_3$)$_2$ | H |
| 6-CH$_3$— | Cl | Cl | OCH$_2$CH$_2$CH$_3$ | H |
| 6-CH$_3$— | Cl | Cl | OCH$_2$CH$_2$CH$_2$—CH$_3$ | H |
| 5-CH$_3$— | Cl | Cl | OCH$_2$CH(CH$_3$)$_2$ | H |

EXAMPLE 2

Using the procedure of Example 1 with 2-acetylcyclopentanone and the approprite arylhydrazine, the following 2-aryl-3-methyl-2,4,5,6-tetrahydrocyclopentapyrazoles of Formula 1 can be prepared:

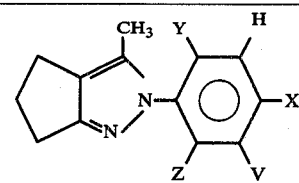

| Y | X | V | Z | M.P. |
|---|---|---|---|---|
| H | Cl | H | H | 72–75° |
| H | Br | H | H |  |
| H | CH$_3$O | H | H |  |
| H | CN | H | H | 159–162° |
| F | F | H | F |  |
| Cl | Cl | H | H |  |
| F | Br | H | H |  |
| F | Cl | H | H | 80–81° |
| F | CH$_3$O | H | H |  |
| F | CN | H | H |  |
| F | F | H | H |  |
| F | I | H | H |  |
| H | I | H | H |  |
| Cl | Cl | Cl | H |  |
| F | F | F | H |  |
| Cl | Cl | OCH$_3$ | H | 149–151° |
| Cl | Cl | OC$_2$H$_5$ | H |  |
| Cl | Cl | OCH(CH$_3$)$_2$ | H |  |
| Cl | Cl | OCH$_2$CH$_2$CH$_3$ | H |  |
| Cl | Cl | OCH$_2$CH$_2$CH$_2$CH$_3$ | H |  |
| Cl | Cl | OCH$_2$CH(CH$_3$)$_2$ | H |  |

Using the procedure of Example 1 with 2-acetylcycloheptanone and the appropriate arylhydrazine, the following 2-aryl-3-methyl-2,4,5,6,7,8-hexahydrocycloheptapyrazoles of Formula 1 can be prepared:

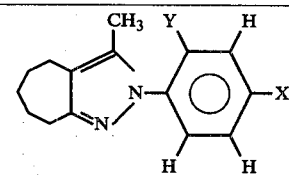

| Y | X |
|---|---|
| H | Cl |
| F | Cl |
| F | Br |
| H | Br |
| H | F |

Formulations

Useful formulations of the compounds of Formula I. can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters, or even less, to several hundred liters per hectare. High strength compositions are primarily used as intermediates for further formulation. The formulations, broadly, contain about 0.05% to 99% by weight of active ingredient(s) and at least one of a) about 0.1% to 20% surfactant(s) and b) about 1% to 99.95% solid or liquid diluent(s). More specifically, they will usually contain these ingredients in the following approximate proportions:

|  | Percent by Weight | | |
| --- | --- | --- | --- |
|  | Active Ingredient | Diluent(s) | Surfactant(s) |
| Wettable Powders | 5–90 | 1–94 | 1–10 |
| Oil Suspensions, Emulsions, Solutions (including Emulsifiable Concentrates) | 5–50 | 40–95 | 0–15 |
| Aqueous Suspensions | 5–50 | 40–94 | 1–20 |
| Dusts | 0.05–25 | 70–99.95 | 0–5 |
| Granules and Pellets | 0.05–95 | 1–99.95 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Edn., Dorland Bookds, Caldwell, N.J. Suitable diluents include finely divided or granular solids classified as attapulgites, botanicals, calcites, diatomites, dolomites, gypsum, kaolinites, limestones, mica, montmorillonoids, phosphates, pyrophyllites, sulfur, sand, talcs, tripolites, vermiculite and synthetics. These synthetics can include precipitated, hydrated silicon dioxide; precipitated, hydrated calcium silicate; precipitated calcium carbonate and synthetic organics. The more absorptive diluents are preferred for wettable powders and the denser ones for dusts. Typical liquid diluents and solvents are described in Marsden, "Solvents Guide", 2nd Edition, Interscience, New York. 1950. Solubility under 0.1% is preferred for suspension concentrates; solution concentrates are preferably stable against phase separation at 0° C. "McCutcheon's Detergents and Emulsifiers 1975 Annual", MC Publ. Corp., Ridgewood, N. J., as well as Sisely and Wood, "Encyclopedia of Surface Active Agents", Chemical Publ. Co., New York, 1964, list surfactants and recommended uses. All formulations can contain minor amounts of additives to reduce foam, caking, corrosion, microbiological growth, etc., or to mark visually the area that has been treated.

It is sometimes desirable to add ingredients to reduce the volatility or control the release rate of some of the compounds of this invention. Those additives can include film forming materials such as polyvinyl pyrrolidones of molecular weights from about 20,000 to about 100,000; polyvinyl alcohols of molecular weight from about 20,000 to about 150,000; and polyoxyethylenes of moelcular weights from about 100,000 to about $5 \times 10^6$. These are a few examples of film forming additives. Any material which forms a film over solid active ingredient in the formulation preparation or a film over the active when sprayed and dried from a liquid formulation can be used. Other methods to reduce volatility or control the release rate may include the incorporation of the compounds of this invention into resins, waxes, gums, rubbers, or the like, and then preparing formulations, as has been described above, for these combinations.

Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

Granules may be made in several ways. For example, the active ingredient may be sprayed onto a preformed granular carrier. Suitable granular carriers include those suitable diluents listed earlier having a particle size range from USS Sieve No. 200 (74 microns) to USS Sieve No. 10 (2000 microns). The preferred particle size range is from USS Sieve No. 140 (105 microns) to USS SIeve No. 20 (840 microns). Depending on the nature of the carrier, the active ingredient may remain on the surface of the carrier or be absorbed into the carrier. Usually, when the active ingredient remains on the surface of the carrier, a binding agent is used to hold the active ingredient on the surface. The binding agent should bind the active ingredient to the surface well enough so that no more than 10% of the active ingredient is removed during normal shipping and handling operations. Suitable binding agents include materials which are at least partially soluble in any liquid used in the manufacture of the granular formulation and which adhere to the granular surface. Water-soluble binders are preferred. Suitable binders include, but are not limited to, water-soluble polymers such as polyvinyl alcohols of molecular weights from about 20,000 to about 150,000; polyvinylpyrrolidones of moelcular weights from about 20,000 to about 100,000 and polyoxyethylenes of molecular weights from about 100,000 to about $5 \times 10^6$. Other suitable binders include ligninsulfonates, starches, sugars and certain surface active agents listed in "McCutcheon's Detergent and Emulsifiers 1975 Annual", MC Publ. Corp., Ridgewood, N. J.

The active ingredient may be sprayed as a solution in a suitable solvent, which may or may not be removed from the formulation. If the active ingredient is a liquid, it may be sprayed onto or mixed with the carrier directly. If it is a solid, it may be melted and applied directly as a liquid. If very low strength granules are desired, the active ingredient may be vaporized onto the carrier. Granules may also be prepared by agglomeration techniques. For example, the active ingredient and a finely divided solid diluent may be mixed and agglomerated by techniques known in the art such as spraying with a liquid in a fluidized bed or pan granulator. The active ingredient and diluent may also be mixed with other formulation ingredients and pelletized. The pellets may then be crushed to a desired granular size. Pellets may be made by spraying the active material upon preformed granular carriers or by agglomeration techniques.

See J. E. Browning, "Agglomeration", *Chemical Engineering*, Dec. 4, 1967, pp. 147ff. and "Perry's Chemical Engineer's Handbook", 4th. Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, March 14, 1967, Col. 5 Line 43 through Col. 7 Line 62 and Ex. 8, 12, 15, 39, 41, 52, 53, 58, 132, 138–140, 162–164, 166, 167, 169–182.

H. Gysin and E. Knüsli, U.S. Pat. No. 2,891,855. June 23, 1959, Col. 3 Line 66 through Col. 5 Line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

EXAMPLE 4

| Granule | |
|---|---|
| 2-(4-chlorophenyl)-3-methyl-4,5,6,7-tetrahydro-2H-indazole | 10% |
| attapulgite granules (low volatile matter, 0.71–0.30 mm; U.S.S. #25–50 sieves) | 90% |

The active ingredient is warmed to approximately 90° C and sprayed upon dedusted and pre-warmed to attapulgite granules which are being tumbled in a double-cone blender. The granules are then allowed to cool and are packaged.

EXAMPLE 5

| Solution | |
|---|---|
| 2-(2,4-difluorophenyl)-3-methyl-4,5,6,7-tetrahydro-2H-indazole | 20% |
| dimethylformamide | 80% |

The ingredients are combined and stirred to produce a solution, which can be used for low-volume applications.

EXAMPLE 6

| Extruded Pellet | |
|---|---|
| 2-(4-chloro-2-fluorophenyl)-3-methyl-4,5,6,7-tetrahydro-2H-indazole | 1% |
| anhydrous sodium sulfate | 10% |
| crude calcium ligninsulfonate | 5% |
| sodium alkylnaphthalenesulfonate | 1% |
| polyoxyethylene (4 × 10$^6$ average molecular wt.) | 1% |
| calcium/magnesium bentonite | 82% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled. All compounds of this invention may be formulated in this manner.

EXAMPLE 7

| Emulsifiable Concentrate | |
|---|---|
| 2-(4-chlorophenyl)-3-methyl-4,5,6,7-tetrahydro-2H-indazole | 25% |
| blend of oil soluble sulfonates and polyoxyethylene ethers | 4% |
| xylene | 71% |

The ingredients are combined and stirred until solution is complete. A fine screen filters is included in packaging operation to insure the absence of any extraneous undissolved material in the product.

EXAMPLE 8

| Aqueous Suspension | |
|---|---|
| 2-(4-chloro-2-fluorophenyl)-3-methyl-4,5,6,7-tetrahydro-2H-indazole | 40.0% |
| polyacrylic acid thickener | 0.3% |
| dodecylphenol polyethylene glycol ether | 0.5% |
| disodium phosphate | 1.0% |
| monosodium phosphate | 0.5% |
| polyvinyl alcohol | 1.0% |
| pentachlorophenol | 0.4% |
| water | 56.3% |

The ingredients are ground together in a sand mill to produce particles essentially all under five microns in size.

EXAMPLE 9

| Wettable Powder | |
|---|---|
| 2-(4-chloro-2-fluorophenyl)-3-methyl-4,5,6,7-tetrahydro-2H-indazole | 50% |
| sodium alkylnaphthalenesulfonate | 2% |
| sodium ligninsulfonate | 2% |
| synthetic amorphous silica | 3% |
| kaolinite | 43% |

The ingredients are thoroughly blended, passed through an air mill to produce an average particle size under 15 microns, reblended, and sifted through a U.S.S. No. 50 sieve (0.3 mm opening) before packaging.

EXAMPLE 10

| High Strength Concentrate | |
|---|---|
| 2-(4-chloro-2-fluorophenyl)-3-methyl-4,5,6,7-tetrahydro-2H-indazole | 99% |
| trimethylnonyl polyethylene glycol ether | 1% |

The surfactant is sprayed upon the active ingredient in a blender and the mixture sifted through a U.S.S. No. 40 sieve (0.42 mm openings) prior to packaging. The concentrate may be formulated further for practical use.

EXAMPLE 11

| Low Strength Granule | |
|---|---|
| 2-(4-chlorophenyl)-3-methyl-4,5,6,7-tetrahydro-2H-indazole | 0.5% |
| polyvinylpyrrolidone | 1% |
| attapulgite granuls (low volatile matter, 0.59–0.25 mm; U.S.S. #30–60 mesh size) | 98.5% |

Forty grams of a solution containing 2.5% 2-(4-chlorophenyl)-3-methyl-4,5,6,7-tetrahydro-2H-indazole and 5% polyvinylpyrrolidone dissolved in methyl alcohol are slowly atomized onto a fluidized bed of attapulgite granules (197 gm). Fluidization of the granules is continued after atomization is complete and until all the methyl alcohol is evaporated from the granules. The granules are packaged for use.

EXAMPLE 12

| Extruded Pellet | |
|---|---|
| 2-(4-chlorophenyl)-3-methyl-2,4,5,6-tetrahydrocyclopentapyrazole | 25% |
| anhydrous sodium sulfate | 10% |

-continued

| Extruded Pellet | |
|---|---|
| crude calcium ligninsulfonate | 5% |
| sodium alkylnaphthalenesulfonate | 1% |
| calcium/magnesium bentonite | 59% |

The ingredients are blended, hammer milled and moistened with about 10–12% water. The mixture is then extruded as cylinders about 3 mm in diameter which are cut to be about 3 mm long. These pellets may be used directly after drying or the dried pellets may be crushed to pass a U.S.S. #20 sieve (0.84 mm opening). The pellets retained on a U.S.S. #40 sieve (0.42 mm openings) may be packaged for use and the fines recycled.

EXAMPLE 13

| Granule | |
|---|---|
| 2-(4-chloro-2-fluorophenyl)-3-methyl 2,4,5,6-tetrahydrocyclopentapyrazole | 2% |
| attapulgite granules (low volatile matter, 0.71–0.30 mm; U.S.S. #25–50 mesh sieves) | 98% |

The active ingredient is warmed to approximately 100° C and sprayed upon the dedusted and pre-warmed granules in a double cone blender. The granules are allowed to cool and are packaged for use.

EXAMPLE 14

| Low Strength Granules | |
|---|---|
| 2-(4-chlorophenyl)-3-methyl-4,5,6,7-tetrahydro-2H-indazole | 0.2% |
| anhydrous sodium sulfate | 10.0% |
| crude calcium ligninsulfonate | 5.0% |
| sodium alkylnaphthalenesulfonate | 1.0% |
| finely divided attapulgite clay | 83.8% |

The ingredients are blended, hammer milled and placed in a fluidized bed granulator. Water is aspirated into the fluidized bed of powder until small granules are formed. Water aspiration is then stopped, but fluidization is continued to dry the formed granules. The granules are removed from the granulator and screened to pass a USS Sieve No. 20 (0.42 mm openings). Granules retained on a USS Sieve No. 40 (0.42 mm openings) are packaged for use. Granules larger than 0.84 mm are ground and recycled. Fines smaller than 0.42 mm are also recycled.

EXAMPLE 15

| Extruded Pellet | |
|---|---|
| 2-(2,4-difluorophenyl)-3-methyl-4,5,6,7-tetrahydro-2H-indazole | 0.1% |
| anhydrous sodium sulfate | 10.0% |
| crude calcium ligninsulfonate | 5.0% |
| sodium alkylnaphthalenesulfonate | 1.0% |
| polyoxyethylene (4 × 10⁶ average molecular wt) | 1.0% |
| calcium/magnesium bentonite | 82.9% |

The ingredients are blended, hammer milled and then moistened with about 12% water. The moist mixture is extruded as cylinders about 1 mm diameter and 2 mm long. These small pellets are dried and packaged. They are applied directly.

EXAMPLE 16

| Low Strength Granules | |
|---|---|
| 2-(4-chloro-2-fluorophenyl)-3-methyl-4,5,6,7-tetrahydro-2H-indazole | 0.05% |
| dimethylformamide | 5.00% |
| attapulgite granules (low volatile matter, 0.59–0.25 mm; USS Sieve No. 30–60) | 94.95% |

The active ingredient is dissolved in dimethylformamide. This solution is very slowly atomized onto a rapidly tumbling bed of the attapulgite granules. After application of the active ingredient is complete, the formulation is blended for a few additional minutes. The dimethylformamide is not removed from the formulation. The granules are packaged for use.

EXAMPLE 17

| Emulsifiable Concentrate | |
|---|---|
| 2-(4-chlorophenyl)-3-methyl-4,5,6,7-tetrahydro-2H-indazole | 20% |
| blend of oil-soluble sulfonate with polyoxyethylene ethers | 6% |
| aromatic hydrocarbon solvent with a closed cup flash point between 100 and 115° F. | 74% |

The ingredients are combined and stirred until solution is complete. The slution is filtered prior to packaging through a fine screen filter to remove any extraneous undissolved material.

EXAMPLE 18

| Low Strength Granules | |
|---|---|
| 2-(4-chloro-2-fluorophenyl)-3-methyl 4,5,6,7-tetrahydro-2H-indazole | 0.1% |
| sodium ligninsulfonate | 5.0% |
| preformed sand granules having a particle size distribution from USS Sieve No. 140 (105 microns) to USS Sieve No. 50 (297 microns) | 94.9% |

The active ingredient and sodium ligninsulfonate are dissolved in methyl alcohol. This solution is slowly sprayed onto a tumbling bed of the sand granules. After spraying is complete, the tumbling granules are warmed to remove the methyl alcohol. The resulting granules are packaged for use.

Compositions can contain, in addition to the active ingredients of this invention, other conventional agricultural chemicals such as fertilizers, plant growth modifiers or herbicides.

For example, the compounds of Formula I can be combined with the following herbicides:
1. 5-tert-butyl-3-(2,4-dichloro-5-isopropoxyphenyl)-1,3,4-oxadiazol-2-one;
2. 6-methylthio-2,4-bis(ethylamino)-s-triazine;
3. 3-isopropyl-(1H)-benzo-2,1,3-thiodiazin-4-one-2,2-dioxide;
4. 2,4-dichlorophenoxyacetic acid and related esters and salts.

Combinations with wheat herbicides:
1. 2,4-dichlorophenoxyacetic acid and related esters and salts;
2. S-(2,2,3-trichloroallyl)-diisopropylthiocarbamate;
3. Methyl 2-[4-(2,4-dichlorophenoxy(phenoxy)]-propanoate;

4. 1,2-dimethyl-3,5-diphenyl-1H-pyrazolium methyl sulfate;

5. 4-chloro-2-butynyl 3-chlorocarbanilate.

The compounds of Formula I can also be combined with other herbicides and are particularly useful in combination with bromacil [3-(sec-butyl)-5-bromo-6-methyluracil], diuron [3-(3,4-dichlorophenyl)-1,1-dimethylurea], 3-cyclohexyl-1-methyl-6-dimethylamino-s-triazine-2,4(1H,3H)-dione, paraquat [1,1'-dimethyl-4,4'-bipyridinum ion], m-(3,3-dimethylureido) phenyl tert-butylcarbamate, 2-methyl-4-chlorophenoxyacetic acid, its salts or esters, 4-amino-6-tert-butyl-3-methylthioas-triazin-5(4H)-one, aryl 4-nitrophenyl ethers such as 2,4,6-trichlorophenyl 4-nitrophenyl ether and 2,4-dichlorophenyl 4-nitrophenyl ether for controlling a broad spectrum of weeds.

The agricultural chemicals listed above are exemplary of the compounds which can be mixed with the active compounds and are not intended to limit the invention in any way.

Utility

The compounds of Formula I are useful for the selective preemergence control of undesired vegetation in crops such as rice, and wheat. These compounds also have utility for the postemergence control of weeds in certain crops, for example, rice. Furthermore, compounds of this invention can be used as directed treatments for the pre- or post-emergence control of weeds in various crops including soybeans, peanuts, cotton, garden beans and row-planted rice.

The compounds of this invention are useful for the control of weeds in transplanted crops such as rice, tobacco, tomatoes, cabbage, sweet potatoes, lettuce, celery, peppers, and eggplant. The treatment may be applied to the soil surface prior to transplanting and the crop transplanted through the treated soil or it may be soil incorporated prior to transplanting and the crop set in the treated soil. It may be applied after the crop is transplanted if care is taken to keep the chemical off the foliage. In addition, these compounds are useful wherever general weed control is required, such as industrial sites, railroad and utility rights-of-way, along fences, building foundations, parking and storage lots, etc.

The precise amount of the compounds of Formula I to be used in any given situation will vary according to the particular end result desired, the use involved, the crop weed species, and soil involved, the formulation used, the mode of application, prevailing weather conditions, foliage density and the like factors. Since so many variables play a role, it is not possible to state a rate of application suitable for all situations. Broadly speaking, the compounds of the invention are used at levels of about 0.05 to about 15 kilograms per hectare, preferably about 0.10 to about 10 kilograms per hectare. The lower rates in this range will generally be selected on lighter soils, soils low in organic matter content, for selective weed control in crops, or in situations where maxiumum persistence is not necessary.

The herbicidal activity of the compounds of this invention was discovered in greenhouse tests, as described below:

EXAMPLE 19

Seeds of crabgrass (Digitaria sp.), barnyardgrass (*Echinochloa crusgalli*), wild oats (*Avena fatua*). Cassia tora, morningglory (*Ipomoea sp.*), cocklebur (*Xanthium sp.*) sorghum, corn, soybean, rice, wheat and nutsedge (*Cyperus rotundus*) tubers were placed in a growth medium and treated preemergence wih the chemicals dissolved in a non-phytotoxic solvent. At the same time, cotton having five leaves (including cotyledonary ones) bush beans with the second trifoliolate leaf expanding, crabgrass with two leaves, barnyardgrass with two leaves, wild oates with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with two leaves, and nutsedge with three-five leaves were sprayed. Treated plants and controls were maintained in a greenhouse for sixteen days, then all species were compared to cotrols and visually rated for response to treatment.

Ratings for compounds treated by this procedure are recorded in Table I.

TABLE I
| COMPOUND | KG PER HECTARE | BUSH BEAN | COTTON | MORNING GLORY | COCKLEBUR | CASSIA | NUTSEDGE | CRABGRASS | BARNYARD GRASS | WILD OATS | WHEAT | CORN | SOYBEAN | RICE | SORGHUM |
|---|---|---|---|---|---|---|---|---|---|---|---|---|---|---|---|
| 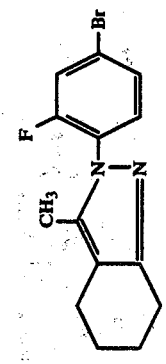 | 0.4 | 9B | 10B | 9B | 10B | 6B | 2B | 2B | 8B | 10B | 9B | 6B | 8B | 3B | 9B | 4B |
| 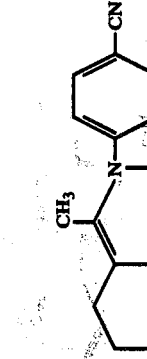 | 0.4 | 9B | 7B | 7B | 4B | 2B | 2B | 3B | 3B | 2B | 1B | 3B | 8B | 4B | 3B |
| 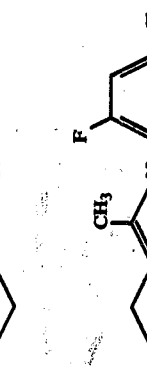 | 0.4 | 9B | 10B | 10B | 8B | 9B | 3B | 3B, 7H | 9B | 6B | 5B | 8B | 9B | 8B | 10B |
| 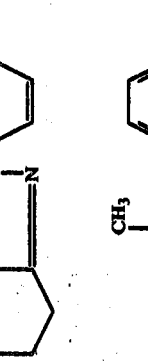 | 0.4 | 9B | 7D, 8B | 3B | 3B | 2B | 2B | 5G, 1B | 8B | 3B | 2B | 3B | 3B | 4B | 7B |
| 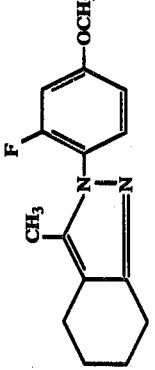 | 2 | 9B | 5B | 6B | 2B | 1B | 2B | 5B | 10B | 2B | 3B | 6B | 5B | 7B | 10B |
AND TABLE I-continued

POST EMERGENCE

| COMPOUND | KG PER HEC- TARE | BUSH BEAN | COT- TON | MORN- ING GLORY | COCKLE- BUR | CAS- SIA | NUTS- EDGE | CRAB- GRASS | BARN- YARD GRASS | WILD OATS | WHEAT | CORN | SOY- BEAN | RICE | SOR- GHUM |
|---|---|---|---|---|---|---|---|---|---|---|---|---|---|---|---|
| ![structure] | | | | | | | | | | | | | | | |
| ![structure] | 2 | 10B | 9B | 9B | 3B | 3B | 4B | 3B, 6H | 10B | 9B | 7B | 8B | 10B | 6B | 8B |
| ![structure] | 0.4 | 9B | 9B | 10B | 5B | 1B | 2B | 9H, 5B | 9B | 1B | 1B | 5B | 6B | 6B | 9B |
| ![structure] | 0.4 | 8B | 9B | 8B | 7B | 3B | 2B | 7B | 9B | 3B | 3B | 7B | 9B | 7B | 7B |
| ![structure] | 0.4 | 7B | 7B | 2B | 1B | 1B | 1B | 1B | 6B | 1B | 2B | 3B | 3B | 3B | 6B |

TABLE I-continued
| COMPOUND | KG PER HECTARE | BUSH BEAN | COTTON | MORNING GLORY | COCKLE-BUR | CASSIA | NUTSEDGE | POST EMERGENCE CRABGRASS | BARNYARD GRASS | WILD OATS | WHEAT | CORN | SOYBEAN | RICE | SORGHUM |
|---|---|---|---|---|---|---|---|---|---|---|---|---|---|---|---|
| 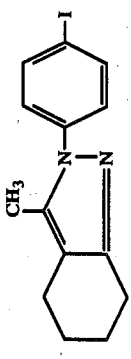 | 0.4 | 6B | 7B | 2B | 1B | 2B | 1B | 1B | 6B | 1B | 1B | 5B | 2B | 2B | 3B |
| 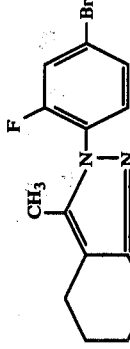 | 0.4 | | | 1C | 1C | 0 | 1C | 3H | 9H, 1C | 7C | 8C | 10E | 2C | 7C | 7C |
| 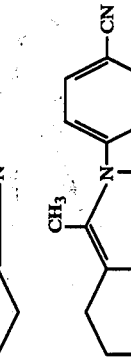 | 0.4 | | | 3H | 0 | 6G | 0 | 0 | 9C | 6C | 6C | 10C | 3H | 5C | 6C |
| 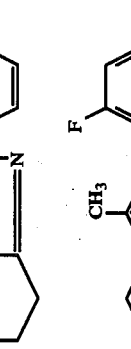 | 0.4 | | | 3G | 3G | 1C | 0 | 9H | 10C | 9C | 9C | 9H, 3C | 8H | 8C | 9H, 3C |
| 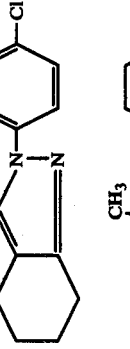 | 0.4 | | | 1C | 0 | 1C | 0 | 0 | 9C | 6G, 1C | 6G, 2C | 9H, 3C | 1C | 1C | 1C |
| 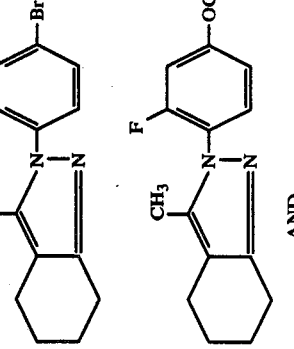 AND | 2 | | | 0 | 0 | 3C | 0 | 8C | 9C | 3G | 4H, 2C | 9H | 5G | 2C | 5C |

TABLE I-continued

POST EMERGENCE

| COMPOUND | KG PER HECTARE | BUSH BEAN | COT-TON | MORN-ING GLORY | COCKLE-BUR | CAS-SIA | NUTS-EDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|---|---|
| [structure: CH₃-C(=N)-N-phenyl-OCH₃ with cyclohexane] | | | | | | | | | | | | | | | |
| [structure: 4-Cl-phenyl-N=N-pyrazole with cyclohexane] | 2 | | 3B | 10E | 6G | 0 | 9C | 10C | 9C | 7C | 9H,2C | 5G | 5C | 8C |
| [structure: 2-Cl,5-OCH₃-phenyl with Cl, pyrazole, cyclohexane] | 0.4 | | 5G | 4G | 3G | 5C | 9H,1C | 9C | 9C | 9C | 9C | 5H | 9C | 9C |
| [structure: 2-F,4-I-phenyl-pyrazole-cyclohexane] | 0.4 | | 0 | 1C | 1C | 0 | 6H,1C | 9C | 8C | 8C | 9C | 0 | 9C | 9H,2C |
| [structure: 4-F-phenyl-pyrazole-cyclohexane] | 0.4 | | 1C | 0 | 0 | 0 | 1C | 7H,2C | 1C | 1C | 4G,1C | 0 | 1C | 1C |
| [structure: 4-I-phenyl-pyrazole-cyclohexane] | 0.4 | | 0 | 0 | 0 | 0 | 3G | 7H,2C | 2C | 2C | 8H,1C | 0 | 1C | 2C |

The plant response ratings above are composed of a number and a letter. The number describes the extent of the response and ranges from zero to ten with zero representing no response, and ten representing 100% response. The letter describes the type of the response, with "B" representing burn, "C" chlorosis-necrosis, "D" defoliation, "E" emergence inhibited, "G" growth retarded, and "H" formative effect (malformation or hormone type).

EXAMPLE 20

The following table, Table II, is presented to further illustrate the biological activity of the compounds of this invention. The data illustrate the herbicidal efficacy of the compounds with selectivity for two important crops, rice and wheat.

The test compounds were applied in a non-phytotoxic solvent to soil pots containing seeds of an intermediate hybrid rice, japonica rice, barnyardgrass (*Echinochloa crusgalli*), morning glory (*Ipomoea sp.*), wheat, wile oats, (*Avena fatua*), downy brome (*Bromus tectorum*), and cheat (*Bromus secalinus*). In addition, wild mustard (*Brassica arvensis*) and Kochia (*Kochia scoparia*) seeds were included in some instances, as were established plantings (post-emergence) of some or all of the species mentioned above. The plants were maintained in a greenhouse (glasshouse), and visual plant response ratings (as described in Example 19) were generally taken three to four weeks after application.

TABLE II

| COMPOUND | Kg ai/hectare | PRE-EMERGENCE |||||||||| POST EMERGENCE ||||||||||
|---|---|---|---|---|---|---|---|---|---|---|---|---|---|---|---|---|---|---|---|---|
| | | NATO INT. Rice | CS-M3 JPN Rice | Barn-yard-grass | Morn-ing Glory | Wheat | Wild Oats | Bromus tectorum | Bromus secalinus | Wild mustard | Ko-chia | NATO INT. Rice | CS-M3 JPN Rice | Barn-yard-grass | Morn-ing Glory | Wheat | Wild Oats | Bromus tectorum | Bromus secalinus | Wild Mustard | Ko-chia |
| [structure: cyclohexane-fused pyrazole with N-(4-OCH₃-phenyl), CH₃] | 1/4 | 0 | 0 | 1G | 0 | | | | | | | 0 | 0 | 0 | 0 | | | | | | |
| AND | 1 | 0 | 0 | 5G | 0 | | | | | | | 0 | 0 | 2C | 0 | | | | | | |
| [structure: cyclohexane-fused pyrazole with N-(4-OCH₃-phenyl), CH₃] | 1/4 | 0 | 0 | 0 | 0 | 0 | 0 | 0 | 0 | 3C | 7C | 0 | 0 | 0 | | 0 | 0 | 0 | 0 | 4B | 9B |
| | 1/2 | 0 | 0 | 0 | 0 | 0 | 0 | 0 | 0 | 4C | 7C | 0 | 0 | 0 | — | 0 | 0 | 0 | 0 | 1B | 9B |
| | 2 | 3G | 1C | 10C | 0 | 0 | 6G | 10C | 9C | — | — | 0 | 0 | 9B | — | 0 | 0 | 0 | 0 | 10B | 10B |
| [structure: cyclohexane-fused pyrazole with N-(4-Cl-phenyl), CH₃] | 1/8 | 0 | 0 | 0 | 0 | 0 | 0 | 0 | 0 | 0 | | 0 | 0 | 0 | 0 | 5B | 0 | 0 | 0 | 0 | |
| | 1/4 | — | 0 | 0 | — | 0 | 0 | 0 | 0 | 0 | | 0 | 0 | 0 | 0 | 5B | 0 | 0 | 1B | 1B | |
| | 1/2 | 0 | 0 | 0 | 0 | 0 | 0 | 0 | 0 | 0 | | 0 | 0 | 0 | 3B | 5B | 1B | 1B | 3B | 3B | |
| | 1 | 0 | 0 | 8C | 0 | 0 | 2C | 2C | 0 | 0 | | 1B | 1B | 3B | 3B | 5B | | | | | |
| [structure: cyclohexane-fused pyrazole with N-(2-OCH₃-4,5-diCl-phenyl), CH₃] | 1/4 | 0 | 0 | 0 | 0 | 0 | 0 | 0 | 0 | 0 | | 0 | 0 | 1B | 0 | 0 | 0 | 0 | 0 | 0 | |
| | 1/2 | 0 | 0 | 0 | 0 | 0 | 0 | 0 | 0 | 0 | | 0 | 2B | 6B | 5B | 0 | 4B | 4B | 1B | 1B | |
| | 1 | 0 | 0 | 0 | 1C | 2C | 2C | 1G | 1G | 1G | | | | 7B | 9B | 1B | 6B | 6B | 3B | 3B | |
| [structure: cyclohexane-fused pyrazole with N-(2-F-4-I-phenyl), CH₃] | 2 | 0 | 0 | 0 | 0 | 0 | 0 | 0 | 0 | | | | | 10B | | | 4B | 8B | 3B | 3B | |
| [structure: cyclohexane-fused pyrazole with N-(2-F-4-Br-phenyl), CH₃] | 1/32 | — | — | — | — | — | — | 0 | 0 | 0 | | | | | | | | | | | |
| | 1/16 | 0 | 0 | 0 | 0 | 0 | 0 | 0 | 0 | 0 | | | | | | | | | | | |
| | 1/4 | 0 | 0 | 8C | 0 | 0 | 0 | 0 | 0 | 6C | | | | | | | | | | | |
| | 1/2 | 0 | 0 | 9C | 10C | 0 | 3C | 0 | 6C | | | | | | | | | | | | |

TABLE II-continued

| COMPOUND | Kg ai/hectare | PRE-EMERGENCE |||||||| POST EMERGENCE ||||||||
|---|---|---|---|---|---|---|---|---|---|---|---|---|---|---|---|---|
| | | NATO INT. Rice | CS-M3 JPN Rice | Barn-yard-grass | Morn-ing Glory | Wheat | Wild Oats | Bromus tectorum | Bromus secalinus | Wild mustard | Kochia | NATO INT. Rice | CS-M3 JPN Rice | Barn-yard-grass | Morn-ing Glory | Wheat | Wild Oats | Bromus tectorum | Bromus secalinus | Wild Mustard | Kochia |
| CH₃, 4-CN-phenyl pyrazoline (cyclohexane fused) | 1/2 | 0 | 0 | 1H | 0 | 0 | 0 | 0 | 0 | | | | | | | | | | | | |
| | 1 | 0 | 0 | 8G | 0 | 0 | 1C | 0 | 0 | | | | | | | | | | | | |
| | 2 | 0 | 0 | 9C | 5G | 1C | 4C | 2G | 3G | | | | | | | | | | | | |
| | 4 | — | 2C | 10C | 5G | 1C | 7C | 5G | 5G | | | | | | | | | | | | |
| CH₃, 2-F-4-Cl-phenyl pyrazoline (cyclohexane fused) | 1/64 | 0 | 0 | 0 | 0 | 0 | 0 | 0 | 0 | | | | | | | | | | | | |
| | 1/32 | 0 | 0 | 0 | 0 | 0 | 0 | 0 | 0 | | | | | | | | | | | | |
| | 1/16 | 0 | 0 | 9C | 0 | 0 | 0 | 0 | 0 | | | | | | | | | | | | |
| | 1/8 | — | — | 10C | 5G | 0 | 9C | 8C | 6C | | | | | | | | | | | | |
| CH₃, 4-Br-phenyl pyrazoline (cyclohexane fused) | 1/4 | 2C | 2C | 10C | 6G | 3G | 9C | 9C | 9C | | | | | | | | | | | | |
| | 1 | 0 | 0 | 5C | 0 | 0 | 0 | 1C | 2C | | | | | | | | | | | | |
| | 4 | 0 | 3G | 10C | 0 | 0 | 4C | 8C | 8C | | | | | | | | | | | | |

It should be noted that, in general, these compounds at a low concentration virtually eliminated the undesirable vegetation, e.g., barnyardgrass, but had relatively little effect on the crops, e.g., rice. In instances where the application rates were too low to demonstrate herbicidal activity, reference may be made to Table I.

EXAMPLE 21

The following table, Table III, is presented to additionally illustrate the biological activity of the compounds of the present invention. The data illustrate the herbicidal efficacy of the compounds with selectivity for rice in paddy culture.

A rice paddy was constructed using a tub containing soil and barnyardgrass (*Echinochloa crusgalli*) seeds, and japonica rice plants which were transplanted into the paddy soil when in the three to four leaf stage. The water level was maintained a few centimeters above the soil surface. The test sample was applied directly into the paddy water, and plant response ratings (as described in Example 19) were taken about three weeks later.

TABLE III

| COMPOUND | Rate, kg ai/ha | Japonica Rice | Barnyardgrass |
|---|---|---|---|
| 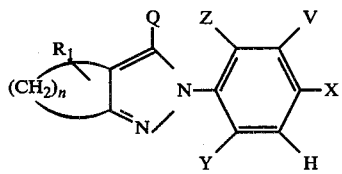 | 1/32 | 0 | 8G |

It should be noted that the undesirable vegetation, e.g., barnyardgrass, was controlled at a very low application rate with little or no injury to the crop, e.g., rice.

What is claimed is:

1. A compound of the formula (I)

where
$n$ is 3, 4 or 5;
$R_1$ is hydrogen or methyl;
Q is methyl;
X is fluorine, chlorine, bromine, iodine, cyano or methoxy;
Y is hydrogen, fluorine or chlorine;
Z is hydrogen or fluorine; and
V is hydrogen, fluorine or chlorine; with the proviso that
  a. when $n$ is 3, $R_1$ is hydrogen; and when V is fluorine or chlorine, X is fluorine, chlorine or bromine and Z is hydrogen;
  b. when $n$ is 4 and V is fluorine or chlorine, X is fluorine, chlorine or bromine and Z is hydrogen; and
  c. when $n$ is 5, $R_1$ is hydrogen, Y is hydrogen or fluorine, Z and V are hydrogen and X is fluorine, chlorine or bromine.

2. A compound of claim 1 wherein $R_1$ is hydrogen and $n$ is 4.
3. A compound of claim 1 wherein Y is hydrogen or fluorine, V is hydrogen and Z is hydrogen.
4. A compound of claim 1 wherein $n$ is 4, $R_1$ is hydrogen, X is fluorine, chlorine or bromine, Y is hydrogen or fluorine, V is hydrogen and Z is hydrogen.
5. A compound of claim 1, 2-(4-chloro-2-fluorophenyl)-3-methyl-4,5,6,7-tetrahydro-2H-indazole.
6. A compound of claim 1, 2-(4-bromo-2-fluorophenyl)-3-methyl-4,5,6,7-tetrahydro-2H-indazole.
7. A composition for the control of undesirable vegetation consisting essentially of a herbicidally effective amount of a compound of claim 1 and at least one of (a) a surface-active agent and (b) a solid or liquid diluent.
8. A composition for the control of undesirable vegetation consisting essentially of a herbicidally effective amount of a compound of claim 2 and at least one of (a) a surface-active agent and (b) a solid or liquid diluent.
9. A composition for the control of undesirable vegetation consisting essentially of a herbicidally effective amount of a compound of claim 3 and at least one of (a) a surface-active agent and (b) a solid or liquid diluent.
10. A composition for the control of undesirable vegetation consisting essentially of a herbicidally effective amount of a compound of claim 4 and at least one of (a) a surface-active agent and (b) a solid or liquid diluent.
11. A composition for the control of undesirable vegetation consisting essentially of a herbicidally effective amount of the compound of claim 5 and at least one of (a) a surface-active agent and (b) a solid or liquid diluent.
12. A composition for the control of undesirable vegetation consisting essentially of a herbicidally effective amount of the compound of claim 6 and at least one of (a) a surface-active agent and (b) a solid or liquid diluent.
13. A method for the control of undesirable vegetation comprising applying to the locus of such undesirable vegetation a herbicidally effective amount of a compound of claim 1.
14. A method for the control of undesirable vegetation comprising applying to the locus of such undesirable vegetation a herbicidally effective amount of a compound of claim 2.
15. A method for the control of undesirable vegetation comprising applying to the locus of such undesirable vegetation a herbicidally effective amount of a compound of claim 3.
16. A method for the control of undesirable vegetation comprising applying to the locus of such undesirable vegetation a herbicidally effective amount of a compound of claim 4.
17. A method for the control of undesirable vegetation comprising applying to the locus of such undesirable vegetation a herbicidally effective amount of the compound of claim 5.
18. A method for the control of undesirable vegetation comprising applying to the locus of such undesirable vegetation a herbicidally effective amount of the compound of claim 6.
19. A method for the control of undesirable vegetation in rice, which comprises applying to the locus of such undesirable vegetation a herbicidally effective amount of a compound of claim 1.
20. A method for the control of undesirable vegetation in rice, which comprises applying to the locus of such undesirable vegetation a herbicidally effective amount of the compound of claim 5.

21. The method of claim 19 wherein the undesirable vegetation is barnyardgrass.

22. A method for the control of undesirable vegetation in wheat comprising applying to the locus of such undesirable vegetation a herbicidally effective amount of a compound of claim 1.

23. A method for the control of undesirable vegetation in wheat comprising applying to the locus of such undesirable vegetation a herbicidally effective amount of the compound of claim 5.

24. A method for the control of undesirable vegetation in paddyrice comprising applying to the locus of such undesirable vegetation a herbicidally effective amount of a compound of claim 1.

25. A method for the control of undesirable vegetation in paddyrice comprising applying to the locus of such undesirable vegetation a herbicidally effective amount of the compound of claim 5.

26. A method for the control of undesirable vegetation in transplanted crops comprising applying to the locus of such undesirable vegetation a herbicidally effective amount of a compound of claim 1.

27. A method for the control of undesirable vegetation in transplanted crops comprising applying to the locus of such undesirable vegetation a herbicidally effective amount of the compound of claim 5.

28. The method of claim 24 wherein the undesirable vegetation is barnyardgrass.

29. A compound of the formula

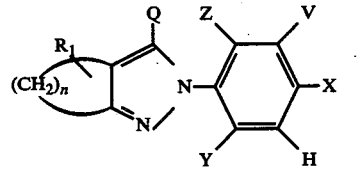

where
$n$ is 3 or 4;
$R_1$ is hydrogen or methyl;
Q is methyl;
X is chlorine;
Y is chlorine;
Z is hydrogen;
V is OR; and
R is alkyl of 1 to 4 carbon atoms, with the proviso that
a. when $n$ is 3, $R_1$ is hydrogen.

30. A compound of claim 29 wherein $R_1$ is hydrogen and $n$ is 4.

31. A composition for the control of undesirable vegetation consisting essentially of a herbicidally effective amount of a compound of claim 29 and at least one of (a) a surface-active agent and (b) a solid or liquid diluent.

32. A method for the control of undesirable vegetation comprising applying to the locus of such undesirable vegetation a herbicidally effective amount of a compound of claim 29.

33. A method for the control of undesirable vegetation in rice, which comprises applying to the locus of such undesirable vegetation a herbicidally effective amount of a compound of claim 29.

34. The method of claim 32 wherein the undesirable vegetation is barnyardgrass.

35. A method for the control of undesirable vegetation in wheat comprising applying to the locus of such undesirable vegetation a herbicidally effective amount of a compound of claim 29.

36. A method for the control of undesirable vegetation in paddyrice comprising applying to the locus of such undesirable vegetation a herbicidally effective amount of a compound of claim 29.

37. The method of claim 35 wherein the undesirable vegetation is barnyardgrass.

38. A method for the control of undesirable vegetation in transplanted crops comprising applying to the locus of such undesirable vegetation a herbicidally effective amount of a compound of claim 29.

39. A composition for the control of undesirable vegetation consisting essentially of a herbicidally effective amount of a compound of claim 30 and at least one of (a) a surface-active agent and (b) a solid or liquid diluent.

40. A method for the control of undesirable vegetation comprising applying to the locus of such undesirable vegetation a herbicidally effective amount of a compound of claim 30.

* * * * *